United States Patent [19]

Harrison

[11] 4,143,047

[45] Mar. 6, 1979

[54] 2-SULFINYL AND 2-SULFONYL OXAZOLES

[75] Inventor: Roger G. Harrison, Farnborough, England

[73] Assignee: Lilly Industries Limited, London, United Kingdom

[21] Appl. No.: 836,284

[22] Filed: Sep. 26, 1977

Related U.S. Application Data

[62] Division of Ser. No. 690,218, May 26, 1976, abandoned.

[30] Foreign Application Priority Data

Jun. 7, 1975 [GB] United Kingdom ............... 24552/75

[51] Int. Cl.$^2$ .......................................... C07D 263/46
[52] U.S. Cl. ................................. 260/307 R; 424/272
[58] Field of Search ..................................... 260/307 R

[56] References Cited

U.S. PATENT DOCUMENTS

| 3,288,860 | 11/1966 | Lyness et al. | 260/302 S |
| 3,888,870 | 6/1975 | Jackson | 260/302 S |
| 4,022,607 | 5/1977 | Jackson | 71/88 |

*Primary Examiner*—Paul M. Coughlan, Jr.
*Attorney, Agent, or Firm*—Charles W. Ashbrook; Everet F. Smith

[57] ABSTRACT

Oxazoles having a sulfinyl or sulfonyl substituent at the 2-position are provided. Such compounds readily react with an alkali metal salt of a secondary amide in a method of making 2-acylamino oxazole derivatives having anti-allergic activity.

3 Claims, No Drawings

2-SULFINYL AND 2-SULFONYL OXAZOLES

This is a division of application Ser. No. 690,218, filed May 26, 1976, now abandoned.

This invention relates to a method of preparing certain novel oxazole derivatives substituted by a 2-acylamino group which possess pharmacological activity.

According to the present invention there is provided a method of preparing a novel oxazole derivative of the formula (I):

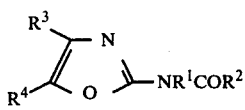
(I)

wherein $R^1$ is $C_{1-10}$ alkyl, $C_{2-6}$ alkenyl, $C_{2-6}$ alkoxyalkyl, $C_{2-6}$ carboxyalky, $C_{1-6}$ haloalkyl, $C_{3-10}$ cycloalkyl, $C_{3-10}$ cycloalkyl-$C_{1-6}$ alkyl, optionally substituted phenyl-$C_{1-6}$ alkyl or optionally substituted phenyl-$C_{2-6}$ alkenyl; and $R^2$ is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, optionally substituted phenyl, optionally substituted phenyl-$C_{1-6}$ alkyl or optionally substituted phenyl-$C_{2-6}$ alkenyl; or $R^1$ and $R^2$ together form a lactam ring having 5 to 7 ring atoms; and wherein $R^3$ and $R^4$ are independently selected from hydrogen, formyl, carboxyl, hydroxy, $C_{1-4}$ hydroxyalkyl, halogen, $C_{1-4}$ alkyl, $C_{3-10}$ cycloalkyl, $C_{3-6}$ acyloxyalkyl or an optionally substituted phenyl group; which method comprises reacting a salt of formula (II):

$$MNR^1COR^2 \quad (II)$$

wherein M is a group IA or IIA metal and wherein $R^1$ and $R^2$ are as previously defined, with a 2-oxazolyl derivative of formula (III):

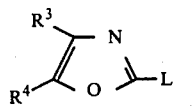
(III)

where L is a leaving group and wherein $R^3$ and $R^4$ are as defined above.

The method of the invention is preferred for compounds of formula (I) wherein $R^1$ is $C_{1-6}$ alkyl, $C_{2-6}$ alkenyl, $C_{2-6}$ alkoxyalkyl, $C_{3-8}$ cycloalkyl, $C_{3-8}$ cycloalkyl-$C_{1-6}$ alkyl, optionally substituted phenyl-$C_{1-6}$ alkyl or optionally substituted phenyl-$C_{2-6}$ alkenyl; $R^2$ is $C_{1-6}$ alkyl, $C_{1-6}$ haloalkyl, $C_{3-6}$ alkenyl, $C_{3-8}$ cycloalkyl, $C_{3-8}$ cycloalkyl-$C_{1-6}$ alkyl, optionally substituted phenyl, optionally substituted phenyl-$C_{1-6}$ alkyl or optionally substituted phenyl-$C_{3-6}$ alkenyl, or $R^1$ and $R^2$ together form a lactam ring having 5 or 6 ring atoms, and wherein $R^3$ and $R^4$ are independently hydrogen, $C_{1-4}$ alkyl, $C_{1-4}$ hydroxyalkyl, $C_{3-8}$ cycloalkyl, $C_{3-6}$ acyloxyalkyl or an optionally substituted phenyl group.

Preferred classes of compounds falling within the scope of the oxazoles defined in formula (I) above are those having one or more of the following characteristics:

(a) $R^1$ is $C_{3-6}$ alkyl, for instance n-butyl and n-propyl;
(b) $R^1$ is $C_{3-4}$ alkenyl;
(c) $R^1$ is phenyl-$C_{1-2}$ alkyl;
(d) $R^2$ is phenyl;
(e) $R^2$ is $C_{1-4}$ alkyl, for instance methyl, n-propyl and i-propyl;
(f) $R^2$ is $C_{3-5}$ cycloalkyl;
(g) $R^1$ and $R^2$ taken together form a lactam ring having 5 carbon atoms;
(h) one or both of the available positions in the oxazole nucleus is substituted by a methyl group;
(i) one or both of the available positions in the oxazole nucleus is substituted by a hydroxymethyl group;
(j) the oxazole nucleus, not considering the acylamino group, is unsubstituted.

The process of the invention is presently most preferred for the preparation of the compound of formula (I) in which $R^1$ is n-butyl, $R^2$ is i-propyl, $R^3$ is methyl and $R^4$ is hydrogen.

The reaction between the salt of formula (II) and the 2-oxazolyl derivative of formula (III) can be accomplished using anhydrous conditions. Any suitable inert solvent may be utilised. Ethereal solvents such as diethyl ether, dioxan or tetrahydrofuran are particularly useful; however, solvents such as dimethylformamide, N-methylpyrrolidone or hexamethylphosphoric triamide may also be used. The reaction can normally be effected at temperatures between 0° and 110° C., preferably between 0° and 40° C., most preferably at room temperature. At these temperatures the reaction will usually be complete after a time of from 1 to 6 hours.

A preferred salt of formula (II) is the lithium derivative which can be conveniently prepared by the reaction of butyl lithium with the appropriate amide of formula $HNR^1COR^2$. This reaction should be carried out under an inert gas atmosphere such as nitrogen and preferably at low temperature, for example, less than $-10°$ C. The presence of a chelating agent such as tetramethylethylene diamine has proved advantageous. Generation of the salt may be effected in situ, if desired, and proceeds with the evolution of butane gas.

The leaving group L in the oxazolyl derivative of formula (III) is preferably a chlorine, bromine or iodine atom, or is a group of formula —SOR or —$SO_2R$, where R is $C_{1-8}$ alkyl, $C_{3-8}$ cycloalkyl, benzyl or phenyl. The identity of suitable L groups will be appreciated by those skilled in the art once it is understood that the reaction of the invention proceeds via the nucleophilic displacement of the L group by the anionic entity $(-)NR^1COR^2$.

Derivatives of formula (III) may be obtained from 2-oxazolones or 2-oxazole-thiones of formula:

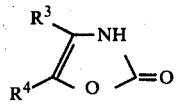
(IV)

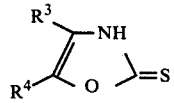
(V)

Such compounds are either known (see, for example, *Berichte* 89, 1748, (1956), *Acta. Chem. Scan.* 23 2879 (1969) and *Bull. Soc. Chim. Belg.* 70, 745 (1961)) or can be prepared from known compounds by conventional procedures.

If it is desired to prepare derivatives of formula (III) in which L is chlorine, bromine or iodine, a compound of formula (IV) or (V) may be reacted with phosphorous pentachloride, phosphorous oxychloride, phosphorous pentabromide or phosphorous triiodide, etc. (see, for examle, Berichte, 92, 1928 (1959)) in the presence of an acid acceptor such as triethylamine, to yield the corresponding chloro, bromo or iodo derivative directly.

Compounds of formula (III) in which L is —SOR or —SO$_2$R can be prepared from the corresponding alkylthio derivatives, i.e. where L is —SR, by treatment with the appropriate amount of oxidising agent, preferably 3-chloroperbenzoic acid. The derivatives may be prepared by alkylation of the corresponding thione of formula (V), preferably by generating the thiolate anion with sodium or sodium hydride.

Compounds of formula (III), except for a small number of exceptions (see, for instance, Berichte 92 1928, (1959), Chemical Abstracts 79 P126485m and 65 7159h) are novel and are provided in a further aspect of the invention.

According to a further aspect of the invention there is provided a compound of formula (III):

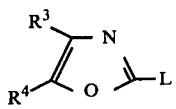

wherein R$^3$ and R$^4$ are as defined previously and where L is bromine or iodine or is a group of formula —SOR or —SO$_2$R, where R is C$_{1-8}$ alkyl, C$_{3-8}$ cycloalkyl, benzyl or phenyl; provided that when L is iodine, R$^3$ and R$^4$ cannot both be phenyl.

Compounds of formula (I) have been shown to be useful in the prophylactic and therapeutic treatment of immediate hypersensitivity diseases including asthma and in the alleviation of status asthmaticus. In certain cases the compounds have been found to be useful in diseases in which excessive amounts of prostaglandins are released and as a respiratory stimulant. The compounds have low toxicity.

The compounds produced according to the present invention may be administered by various routes and for this purpose may be formulated in a variety of forms. Thus the compounds of formula (I) may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I). Dosages of from 0.5 to 300 mg/kg per day, preferably 0.5 to 20 mg/kg of active ingredient may be administered although it will, of course, readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The invention will now be further illustrated with references to the following Examples. Examples 1 to 4 illustrate the preparation of various intermediates of formula (III) whereas Examples 5 to 131 illustrate the utilisation of these intermediates in the process of the invention. The abbreviations "THF" and "HMPA" are used to denote tetrahydrofuran and hexamethylphosphoric triamide respectively.

EXAMPLE 1

2-Chloro-5-phenyloxazole

5-Phenyl-2(3H)-oxazolethione (Acta. Chem. Scand. 23 2879 (1969)) (19.6 g, 0.11 m) and phosphorous oxychloride (70 ml) were stirred with cooling during the cautious addition of triethylamine (12.4 g, 0.123 m). The mixture was then heated under reflux for 20 hours, excess reagents removed under reduced pressure and the residue distilled in vacuo to give the title product as a colourless oil which solidified on standing, b.p. 96°–8° C/0.6 mm, m.p. 34° C.

EXAMPLE 2

4,5-Dimethyl-2-methylthiooxazole 4,5-Dimethyl-2(3H)-oxazolethione [Bull. Soc. Chim. Belg. 70, 745, (1961)] (37.5 g, 0.29 m) in 2N aqueous sodium hydroxide (150 ml) was stirred at room temperature during the dropwise addition of dimethyl sulphate (40.0 g, 0.317 m). The mixture was stirred for 4 hours at room temperature and then warmed to 50° C, cooled, and the aqueous phase extracted with diethyl ether. Evaporation of the solvent and distillation of the residue under reduced pressure gave 33.85 g (81%) of the title product as a pale yellow oil, b.p. 82° C./13 mm.

Analysis: Found: C: 50.39; H: 6.20; N: 10.03; O: 11.30; S: 22.35%. C$_6$H$_9$NOS requires: C: 50.32; H: 6.33; N: 9.78; O: 11.17; S: 22.39%.

Similarly, there were prepared:

4-Methyl-2-methylthiooxazole (Arch. Pharm. 301 (3) 186 (1968).
4-Ethyl-2-methylthiooxazole, b.p. 72° C. (airbath)/14 mm.
5-Methyl-2-methylthiooxazole, b.p. 66° C. (airbath)/11 mm.
2-Methylthio-4-phenyloxazole, [Zh. Obshch. Khim. 33 1507 (1963)]
5-Ethyl-2-methylthiooxazole, b.p. 75° C. (airbath)/15 mm.
2-Ethylthiooxazole, [Phytopathology, 56 (8) 929 (1966)]
2-n-Butylthio-4-methyloxazole, b.p. 98° C./10 mm.
2-n-Hexylthio-4-methyloxazole, b.p. 124° C./10 mm.
2-Cyclohexylthio-4-methyloxazole, b.p. 66°–68°/8 mm.
4-Methyl-2-phenylmethylthiooxazole, b.p. 114°/1 mm.
4,5-Diphenyl-2-phenylthiooxazole [Tetrahedron, Suppl. No. 8 Pt. 1,305 (1966)]

was prepared by the literature method.

EXAMPLE 3

4-Methyl-2-methylsulphinyloxazole

4-Methyl-2-methylthiooxazole (6.06 g, 0.047 m) in dry chloroform (50 ml) was cooled to 0° C. with vigorous stirring and anhydrous sodium carbonate (6.06 g, 0.057 m) added. 96% 3-Chloroperbenzoic acid (8.90 g, 0.0495 m) in dry chloroform (100 ml) was then added dropwise over 45 minutes and the mixture stirred for a further 45 minutes at 0° C. Solid sodium sulphite (2.0 g) was added and the mixture allowed to warm to room temperature. The mixture was then filtered, the filtrate evaporated and the resulting oil was distilled under vacuum to give the title compound as a colourless oil 6.48 g (95%), b.p. (airbath)76° C./0.1 mm.

Analysis: Found: C: 41.54; H: 5.04; N: 9.89; O: 22.24%. $C_5H_7NO_2S$ requires: C: 41.36; H: 4.86; N: 9.65; O: 22.04%.

Similarly prepared were the following:

4,5-Dimethyl-2-methylsulphinyloxazole, b.p. (airbath)96° C./0.1 mm.
4-Ethyl-2-methylsulphinyloxazole, b.p. 82° C./0.1 mm.
5-Ethyl-2-methylsulphinyloxazole, b.p. 85° C./0.1 mm.
5-Methyl-2-methylsulphinyloxazole, b.p. 79° C./0.1 mm.
2-Methylsulphinyl-4-phenyloxazole, m.p. 53° C.
2-Ethylsulphinyloxazole, b.p. 68° C./0.1 mm.
2-n-Butylsulphinyl-4-methyloxazole, b.p. (airbath)82° C./0.1 mm.
2-n-Hexylsulphinyl-4-methyloxazole, b.p. (airbath)90° C./0.1 mm.
2-Cyclohexylsulphinyl-4-methyloxazole, b.p. (airbath) 100° C./0.1 mm.
4-Methyl-2-phenylmethylsulphinyloxazole, m.p. 50° C.
4,5-Diphenyl-2-phenylsulphinyloxazole, m.p. 92° C.

EXAMPLE 4

4,5-Dimethyl-2-Methylsulphonyloxazole 4,5-Dimethyl-2-methylthiooxazole (4.21 g, 0.029 m) in dry chloroform (15 ml) was cooled to 0° C. and anhydrous sodium carbonate (8.0 g, 0.0755 m) added. 88.5% 3-Chloroperbenzoic acid (11.5 g, 0.059 m) in dry chloroform was then added over 45 minutes, and the mixture stirred for a further 45 minutes at 0° C. Solid sodium sulphite (5 g) was then added and the mixture allowed to warm to room temperature. The mixture was then filtered and the filtrate evaporated, the residue being chromatographed on silica using diethyl ether. The resulting solid was recrystallised from ethyl acetate/hexane as the title product, m.p. 42° C.

Similarly prepared were:

4-Methyl-2-methylsulphonyloxazole;
4-Ethyl-2-methylsulphonyloxazole;
5-Ethyl-2-methylsulphonyloxazole;
5-Methyl-2-methylsulphonyloxazole;
2-Methylsulphonyl-4-phenyloxazole;
2-Ethylsulphonyloxazole;
2-n-Butylsulphonyl-4-methyloxazole;
2-n-Hexylsulphonyl-4-methyloxazole;
2-Cyclohexylsulphonyl-4-methyloxazole;
4-Methyl-2-phenylmethylsulphonyloxazole;
4,5-Diphenyl-2-phenylsulphonyloxazole.

EXAMPLE 5

2-(N-butyl-2-methylpropanamido)-5-phenyloxazole n-Butyl-isobutyramide (143 mg., 0.001 m) in dry tetrahydrofuran (5 cc.) was cooled at −15° C. under nitrogen. Tetramethylethylene diamine (0.116 g, 0.001 m) was added, followed by n-BuLi (0.75 cc, of an 8.8% W/V solution in hexane, 0.001 m) stirring was continued for 1½ hours.

Gas evolution was apparent.

2-Chloro-5-phenyloxazole (0.18 g, 0.001 m) in dry THF (1 cc) was then added slowly and the solution allowed to come to room temperature. Stirring was maintained for a further 2 hours and then the product was isolated in ether as a pale yellow oil, 0.22 g. Chromatography gave the title compound which was shown to be homogeneous by tlc. (b.p. 190° C. (air-bath temperature)/0.2 mmHg).

Analysis: $C_{17}H_{22}N_2O_2$ requires: C: 71.39; H: 7.75; N: 9.79%. found: C: 71.64; H: 7.59; N: 9.85%.

Infrared, nmr and tlc confirmed the structure of the product.

EXAMPLE 6

2-(N-Butyl-2-methylpropanamido)-4,5-Diphenyloxazole n-Butyl-isobutyramide (2.06 g, 0.0144 m) in dry THF (20 ml) was stirred at room temperature during the dropwise addition of a 1.445 M solution of n-butyl lithium in hexane (10.0 ml., 0.01445 m). After the addition, the mixture was stirred for 5 minutes, and then 4,5-diphenyl-2-iodooxazole (*Chemical Abstracts* 65 7159h) (5.0 g, 0.0144 m) in dry THF (20 ml) was added dropwise. The mixture was stirred for 6 hours at room temperature and then hydrolysed with water. The solvent was removed in vacuo and the residue extracted with diethyl ether.

Distillation gave the title product as a colourless oil, b.p. (airbath) 200° C./0.1 mm.

Analysis: Found: C: 76.10; H: 7.31; N: 7.62; O: 8.92%. $C_{23}H_{26}N_2O_2$ requires: C: 76.21; H: 7.23; N: 7.73; O: 8.83%.

EXAMPLE 7

2-(N-Butylisobutyramido)-oxazole n-Butyl-isobutyramide(4.93 g, 0.0344 m) in dry diethyl ether (25 ml) was stirred at room temperature under nitrogen during the dropwise addition of a 1.445 M solution of n-butyl lithium (23.8 ml, 0.0344 m). The mixture was stirred for 15 minutes at room temperature and then 2-ethylsulphinyloxazole (5.0 g, 0.0344 m) in dry diethyl ether (25 ml) was added rapidly. The mixture was stirred at room temperature for 3 hours and then hydrolysed with water. The organic phase was washed several times with water, dried over magnesium sulphate and evaporated in vacuo to give a yellow oil. Distillation gave the title product as a colourless oil, b.p. (airbath) 120° C./0.5 mm.

Analysis: Found: C: 62.61; H: 8.74; N: 13.14; O: 15.32%. $C_{11}H_{18}N_2O_2$ requires: C: 62.83; H: 8.63; N: 13.32; O: 15.22%.

EXAMPLE 8

2-(N-Ethyl-acetamido)-4,5-dimethyloxazole

N-Ethyl-acetamide (10.0 g, 0.115 m) in dry butyl hexyl ether (50 ml) was stirred at room temperature under nitrogen during the dropwise addition of a 1.445 M solution of n-butyl lithium in hexane (79.6 ml, 0.115 m). After the addition, the mixture was stirred for 15 minutes and then a solution of 4,5-dimethyl-2-methylsulphonyloxazole (20.0 g, 0.114 m) in dry butyl hexyl ether (50 ml) was added dropwise. The mixture was stirred for 2 hours at room temperature. Isolation of the product and distillation gave a colourless oil, b.p. 61°–62° C/0.3 mm.

Analysis: Found: C: 56.21; H: 8.42; N: 16.41; O: 18.92%. $C_8H_{14}N_2O_2$ requires: C: 56.45; H: 8.29; N: 16.46; O: 18.80%.

EXAMPLE 9

2-(N-Ethyl-acetamido)-4-methyloxazole

N-Ethyl-acetamide (1.18 g, 0.0135 m) in dry dimethylformamide (10 ml) was stirred at room temperature under nitrogen during the portionwise addition of 50% sodium hydride/oil dispersion (0.65 g, 0.0135 m). After the addition, the mixture was warmed to 50° C. and then 4-methyl-2-phenylmethylsulphinyloxazole (3.0 g, 0.0135 m) was added. The mixture was stirred at 50° C. for 5 hours and then hydrolysed with water. The solvent was evaporated in vacuo and the residue extracted with diethyl ether. Column chromatography on silica using ether gave a pale yellow oil which gave the title product as a colourless oil on distillation, b.p. 50°–51° C./0.05 mm.

Analysis: Found: C: 53.92; H: 7.62; N: 17.82; O: 20.59%. $C_7H_{12}N_2O_2$ requires: C: 53.83; H: 7.74; N: 17.94; O: 20.49%.

EXAMPLE 10

2-(N-Methyl-acetamido)-4-methyloxazole

N-Methyl-acetamide (1.02 g, 0.0140 m) in HMPA (10 ml) was stirred at 50° C. under nitrogen during the portionwise addition of 50% potassium hydride/oil dispersion (1.12 g, 0.0140 m). After the addition, the mixture was warmed to 100° C. and 2-n-hexylsulphinyl-4-methyloxazole (3.0 g, 0.0139 m) in HMPA (10 ml) was added and the mixture stirred at 100° C. for 5 hours. The mixture was then hydrolysed with water, solvent removed in vacuo and the product isolated by column chromatography on silica using ether. Recrystallisation from diethyl ether/hexane at −20° C. gave the title product as colourless needles, m.p. 27°–29° C.

EXAMPLE 11

2-(N-Butyl-phenylacetamido)-4-methyloxazole

N-Butyl-phenylacetamide (1.80 g, 0.0094 m) in N-methyl pyrrolidone (10 ml) was stirred at 80° C. under nitrogen during the portionwise addition of a 50% sodium hydride/oil dispersion (0.75 g, 0.0094 m). After the addition, the mixture was warmed to 100° C. and 2-cyclohexylsulphinyl-4-methyloxazole (2.0 g, 0.0094 m) in dry N-methyl pyrrolidone (10 ml) was added. The mixture was stirred at 100° C. for 5 hours and then hydrolysed with water. The solvent was removed in vacuo and the product isolated by column chromatography on silica using ether. Distillation gave the title product as a colourless oil. b.p. 126°–130° C./0.2 mm.

Analysis: Found: C: 70.62; H: 7.60; N: 10.05; O: 11.62%. $C_{16}H_{20}N_2O_2$ requires: C: 70.56; H: 7.40; N: 10.29; O: 11.75%.

EXAMPLE 12

2-(N-s-Butyl-isobutyramido)-4-methyloxazole

N-s-Butyl-isobutyramide (2.30 g, 0.016 m) and tetramethylethylenediamine (1.87 g, 0.016 m) were stirred at 40° C. in sulpholane (20 ml) under nitrogen during the portionwise addition of a 50% potassium hydride/oil dispersion (1.29 g, 0.016 m). After the addition, the mixture was warmed to 70° C. and 2-n-butylsulphinyl-4-methyloxazole (3.0 g, 0.016 m) in sulpholane (20 ml) was added. The mixture was stirred at 70° C. for 6 hours and then hydrolysed with water. Removal of the solvent in vacuo and column chromatography on silica using diethyl ether gave the title compound, which was a colourless oil after distillation in vacuo, b.p. 82° C./0.8 mm.

Analysis: Found: C: 64.04; H: 9.12; N: 12.54; O: 14.34%. $C_{12}H_{20}N_2O_2$ requires: C: 64.26; H: 8.99; N: 12.49; O: 14.27%.

EXAMPLE 13

2-(N-s-Butyl-butyramido)-4-methyloxazole

N-s-Butyl-butyramide (0.99 g, 0.0069 m) in dry dioxan (10 ml) was cooled to 10° C. under nitrogen during the dropwise addition of a 1.445 M solution of n-butyl lithium (4.8 ml, 0.0069 m). The mixture was stirred for 15 minutes at 10° C. and then 4-methyl-2-methylsulphinyloxazole (1.0 g, 0.0068 m) in dry dioxan (10 ml) was added and the mixture allowed to warm to room temperature. It was stirred for 3 hours and then hydrolysed with water. The solvent was removed in vacuo and the ether extract of the residue was chromatographed on silica using ether. The resulting compound (title product) was distilled in vacuo as a colourless oil 0.95 g, b.p. 75°–76° C./0.5 mm.

Analysis: Found: C: 64.02; H: 9.21; N: 12.25; O: 14.31%. $C_{12}H_{20}N_2O_2$ requires: C: 64.26; H: 8.99; N: 12.49; O: 14.27%.

EXAMPLE 14

2-(N-n-Butyl-2-methylpropanamido)-4-methyloxazole n-Butyl-isobutyramide (0.99 g, 0.0069 m) in dry THF (10 ml) was cooled to −20° C. under nitrogen during the dropwise addition of a 1.445 M solution of n-butyl lithium (4.8 ml, 0.0069 m). The mixture was stirred for 20 minutes at −20° C. and then 4-methyl-2-methylsulphinyloxazole (1.0 g, 0.0068 m) in dry THF (10 ml) was added rapidly and the mixture allowed to warm to 0° C. It was stirred at this temperature for 1½ hours then allowed to warm to room temperature and stirred for a further ½ hour. The mixture was hydrolysed with water and the solvent was evaporated under reduced pressure. The residue was extracted with diethyl ether and the extract was evaporated. The resulting oil was chromatographed on silica using ether/hexane. The compound was distilled in vacuo to give the title compound as a colourless oil 1.21 g, (78%), b.p. (airbath) 70° C. at 0.01 mm.

Analysis: Found: C: 64.22; H: 8.76; N: 12.23; O: 14.30%. $C_{12}H_{20}N_2O_2$ requires: C: 64.26; H: 8.99; N: 12.49; O: 14.27%.

EXAMPLES 15 to 131

Similarly prepared were:

2-(N-butyl-pentanamido)-4-methyloxazole, b.p. 88°–91° C./0.2 mm.

2-(N-butyl-hexanamido)-4-methyloxazole, b.p. 102° C./0.3 mm.
2-(N-butyl-2-ethylbutyramido)-4-methyloxazole, b.p. 127° C./2.5 mm.
2-(N-butyl-cyclopropanecarboxamido)-4-methyloxazole, b.p. 97°–100° C./0.5 mm.
2-(N-butyl-cyclohexanecarboxamido)-4-methyloxazole, m.p. 46.5°–48.5° C.
2-(N-butyl-cycloheptanecarboxamido)-4-methyloxazole, b.p. 138°–141° C./1 mm.
2-(N-butyl-3-phenylpropionamido)-4-methyloxazole, b.p. 137°–138° C./0.2 mm.
2-(N-butyl-2-chlorobenzamido)-4-methyloxazole, b.p. 130°–131° C./0.2 mm.
2-(N-butyl-3-chlorobenzamido)-4-methyloxazole, b.p. 145°–147° C./0.4 mm.
2-(N-butyl-2-methoxybenzamido)-4-methyloxazole, b.p. 158°–160° C./0.8 mm.
2-(N-butyl-4-methoxybenzamido)-4-methyloxazole, b.p. 162°–163° C./1.0 mm.
2-(N-butyl-4-toluamido)-4-methyloxazole, b.p. 139°–140° C./0.7 mm.
2-(N-butyl-3-trifluoromethylbenzamido)-4-methyloxazole, b.p. 114°–115° C./0.3 mm.
2-(N-butyl-4-nitrobenzamido)-4-methyloxazole, b.p. 178°–180° C./1.0 mm.
2-(N-methyl-isobutyramido)-4-methyloxazole, b.p. 49°–50° C./0.35 mm.
2-(N-ethyl-butyramido)-4-methyloxazole, b.p. 63°–64° C./0.1 mm.
2-(N-isopropyl-acetamido)-4-methyloxazole, b.p. 75° C./3.0 mm.
2-(N-isopropyl-propionamido)-4-methyloxazole, b.p. 65° C./0.5 mm.
2-(N-isopropyl-butyramido)-4-methyloxazole, b.p. 69° C./0.35 mm.
2-(N-isopropyl-isobutyramido)-4-methyloxazole, b.p. 60°–62° C./0.4 mm.
2-(N-s-butyl-acetamido)-4-methyloxazole, b.p. 64° C./0.6 mm.
2-(N-s-butyl-isobutyramido)-4-methyloxazole, b.p. 82° C./0.8 mm.
2-(N-hexyl-acetamido)-4-methyloxazole, b.p. 90°–92° C./0.08 mm.
2-(N-hexyl-isobutyramido)-4-methyloxazole, b.p. 106°–109° C./1.0 mm.
2-(N-benzyl-acetamido)-4-methyloxazole, b.p. 119°–120° C./0.3 mm.
2-(N-benzyl-propionamido)-4-methyloxazole, b.p. 132°–133° C./0.3 mm.
2-(N-benzyl-butyramido)-4-methyloxazole, b.p. 128° C./0.15 mm.
2-(N-propyl-pentanamido)-4-methyloxazole, b.p. 83°–84° C./0.2 mm.
2-(N-[2-methoxyethyl]acetamido)-4-methyloxazole, b.p. 84° C./0.6 mm.
2-(N-[2-methoxyethyl]propionamido)-4-methyloxazole, b.p. 88° C./0.4 mm.
2-(N-[2-methoxyethyl]butyramido)-4-methyloxazole, b.p. 96° C./0.4 mm.
2-(N-[2-methoxyethyl]-2-ethylbutyramido)-4-methyloxazole, b.p. 98° C./0.4 mm.
2-(N-[2-methoxyethyl]isobutyramido)-4-methyloxazole, b.p. 84°–85° C./0.05 mm.
2-(N-allyl-acetamido)-4-methyloxazole, b.p. 67° C./0.8 mm.
2-(N-allyl-propionamido)-4-methyloxazole, b.p. 75° C./0.8 mm.
2-(N-allyl-benzamido)-4-methyloxazole, b.p. 119° C./0.7 mm.
2-(N-allyl-butyramido)-4-methyloxazole, b.p. 76° C./0.6 mm.
2-(N-allyl-2-ethylbutyramido)-4-methyloxazole, b.p. 83° C./0.65 mm.
2-(N-ethyl-propionamido)-4,5-dimethyloxazole, b.p. 68°–69° C./0.3 mm.
2-(N-ethyl-butyramido)-4,5-dimethyloxazole, b.p. 68°–70° C./0.25 mm.
2-(N-ethyl-isobutyramido)-4,5-dimethyloxazole, b.p. 63°–65° C./0.25 mm.
2-(N-butyl-acetamido)-4,5-dimethyloxazole, b.p. 89°–91° C./1.0 mm.
2-(N-butyl-propionamido)-4,5-dimethyloxazole, b.p. 86°–88° C./0.4 mm.
2-(N-butyl-isobutyramido)-4-cyclohexyloxazole, b.p. 165° C./0.4 mm.*
2-(N-butyl-isobutyramido)-4-butyloxazole, b.p. 140° C./0.5 mm.*
2-(N-butyl-acetamido)-5-acetoxymethyloxazole, b.p. 170° C./0.5 mm.*
5-isobutyroxymethyl-2-(N-butyl-isobutyramido)oxazole, b.p. 180° C./0.5 mm.*
5-cyclohexyl-2-(N-butyl-isobutyramido)oxazole, b.p. 170° C./0.5 mm.
2-(N-cyclopentyl-valeramido)-4-methyloxazole, b.p. 102°–104° C./0.2 mm.
2-(N-2'-methoxyethylcyclopentanecarboxamido)-4-methyloxazole, b.p. 117° C./1.0 mm.
2-(N-2'-phenethyl-propionamido)-4-methyloxazole, b.p. 126° C./0.6 mm.
2-(N-2'-phenethyl-acetamido)-4-methyloxazole, b.p. 122° C./0.5 mm.
2-(N-allyl-isobutyramido)-4-methyloxazole, b.p. 68° C./0.5 mm.
2-(N-β-phenethyl-butyramido)-4-methyloxazole, b.p. 133° C./0.7 mm.
2-(N-β-phenethyl-isobutyramido)-4-methyloxazole, b.p. 128° C./0.65 mm.
4-isobutyroxymethyl-2-(N-butyl-isobutyramido)oxazole, b.p. 180° C./0.5 mm.*
2-(N-butyl-benzamido)-4,5-dimethyloxazole, b.p. 125°–128° C./0.5 mm.
2-(N-butyl-valeramido)-4,5-dimethyloxazole, b.p. 102°–105° C./0.5 mm.
2-(N-butyl-cyclobutanecarboxamido)-4,5-dimethyloxazole, b.p. 105°–107° C./0.5 mm.
2-(N-butyl-butyramido)-4,5-dimethyloxazole, b.p. 95°–98° C./0.5 mm.
2-(N-butyl-3-nitrobenzamido)-4-methyloxazole, b.p. 152°–155° C./0.2 mm.
2-(N-[2-methylbutyl]-butyramido)-4-methyloxazole, b.p. 87° C./0.5 mm.
2-(N-[2-methylbutyl]-propionamido)-4-methyloxazole, b.p. 82°–83° C./0.5 mm.
2-(N-[2-methylbutyl]-isobutyramido)-4-methyloxazole, b.p. 83° C./0.5 mm.
2-(N-pentyl-benzamido)-4-methyloxazole, b.p. 130° C./0.7 mm.
2-(N-cyclohexyl-propionamido)-4-methyloxazole, b.p. 101° C./0.5 mm.
2-(N-ethyl-hexanamido)-4-methyloxazole, b.p. 94°–96° C./0.7 mm.
2-(N-butyl-cyclohexanecarboxamido)-4,5-dimethyloxazole, b.p. 122°–126° C./0.5 mm.
2-(N-butyl-cyclopentanecarboxamido)-4,5-dimethyloxazole, b.p. 112°–116° C./0.5 mm.

2-(N-cyclohexyl-butyramido)-4-methyloxazole, b.p. 118° C./0.7 mm.
2-(N-butyl-3,4-dichlorobenzamido)-4-methyloxazole, b.p. 162°–165° C./1.0 mm.
2-(N-pentyl-butyramido)-4-methyloxazole, b.p. 98° C./0.8 mm.
2-(N-benzyl-benzamido)-4-methyloxazole, m.p. 62° C.
2-(N-benzyl-valeramido)-4-methyloxazole, b.p. 134° C./0.7 mm.
4,5-Dimethyl-2-(N-methyl-acetamido)oxazole, m.p. 40°–42° C.
2-(N-butyl-1-adamantanecarboxamido)-4-methyloxazole, b.p. 160° C./0.3 mm.
2-(N-ethyl-2-ethylbutyramido)-4-methyloxazole, b.p. 71°–2° C./0.3 mm.
2-(N-butyl-4-fluorobenzamido)-4-methyloxazole, b.p. 120°–2° C./0.3 mm.
4-methyl-2-(N-propyl-hexanamido)oxazole, b.p. 96°–8° C./0.4 mm.
4-methyl-2-[N-(1-ethylpropyl)-butanamido]oxazole, b.p. 58°–60° C./0.5 mm.
4-methyl-2-[N-(1-ethylpropyl)-pentamido]oxazole, b.p. 91° C./0.5 mm.
2-(N-pentyl-propanamido)-4-methyloxazole, b.p. 68° C./0.05 mm.
2-(N-pentyl-isobutyramido)-4-methyloxazole, b.p. 86°–7° C./0.4 mm.
2-(N-butyl-isobutyramido)-4-ethyloxazole, b.p. 140° C./0.5 mm.*
2-(N-isopropyl-pentanamido)-4-methyloxazole, b.p. 77° C./0.3 mm.
2-(N-butyl-dichloroacetamido)-4-methyloxazole, b.p. 112°–4° C./0.8 mm.
2-(N-p-chlorobenzyl-isobutyramido)-4-methyloxazole, b.p. 136° C./0.7 mm.
2-(N-hexyl-propanamido)-4-methyloxazole, b.p. 106°–8° C./1.0 mm.
2-(N-butyl-chloroacetamido)-4-methyloxazole, b.p. 96°–8° C./1.0 mm.
2-(N-butyl-isobutyramido)-4-methyl-5-hydroxyoxazole**
(−) 2-(N-but-2-yl-butanamido)-4-methyloxazole, b.p. 86°–9° C./1.2 mm.
(+) 2-(N-but-2-yl-butanamido)-4-methyloxazole, b.p. 85°–8° C./1.5 mm.
2-(N-butyl-N-isobutyramido)-4-hydroxymethyloxazole, b.p. 185° C./0.3 mm.*
2-(N-cyclohexyl-isobutanamido)-4-methyloxazole, b.p. 108° C./0.8 mm.
2-(N-benzyl-hexanamido)-4-methyloxazole, b.p. 144° C./0.6 mm.
2-(N-butyl-4-chlorobutanamido)-4-methyloxazole, b.p. 124°–8° C./1.2 mm.
2-(N-butyl-isobutyramido)-4-p-chlorophenyloxazole, b.p. 200° C./0.5 mm.*
2-(N-butyl-isobutyramido)-5-methyloxazole, b.p. 100° C./0.1 mm.*
1-(4-methyl-oxazol-2-yl)-2-oxo-hexahydro-1H-azepine, b.p. 130° C./0.1 mm.*
2-(N-cyclopentyl-isobutyramido)-4-methyloxazole, m.p. 73° C.
D(−) 2-(N-butyl-2-methylbutanamido)-4-methyloxazole, b.p. 88°–92° C./0.6 mm.
L(+) 2-(N-butyl-2-methylbutanamido)-4-methyloxazole, b.p. 88°–91° C./0.6 mm.
2-(N-butyl-2-methylbutanamido)-4-methyloxazole, b.p. 82°–5° C./0.2 mm.
2-N-(butylisobutyramido)-5-phenyloxazole, b.p. 190° C./0.2 mm.*
2-(N-cinnamyl isobutyramido)-4-methyloxazole, b.p. 152°–156° C./1.0 mm.
2-[N-(4-methylbenzyl)isobutyramido]-4-methyloxazole, b.p. 120°–4° C./0.3 mm.
2-[N-(3-methylbenzyl)isobutyramido]-4-methyloxazole, b.p. 118°–122° C./0.3 mm.
2-(N-butyl-heptanamido)-4-methyloxazole, b.p. 106°–8° C./0.05 mm.
2-(N-butyl-cyclopentylacetamido)-4-methyloxazole, b.p. 124°–6° C./0.8 mm.
2-(N-cyclohexylmethyl-isobutanamido)-4-methyloxazole, b.p. 122°–4° C./0.8 mm.
2-[N-(4-methoxybenzyl)isobutyramido]-4-methyloxazole, b.p. 145°–8° C./0.4 mm.
2-(N-butyl-cinnamamido)-4-methyloxazole, b.p. 200° C./0.2 mm.
2-[N-(3-carboxypropyl)octanamido]-4-methyloxazole, b.p. 200° C./0.2 mm.
2-[N-(3-chloropropyl)pentanamido]-4-methyloxazole, b.p. 118°–122° C./0.7 mm.
2-[N-(3-chloropropyl)isobutyramido]-4-methyloxazole, b.p. 99°–102° C./0.5 mm.
2-(N-butyl-but-2-enamido)-4-methyloxazole, b.p. 150° C./0.02 mm.
2-(N-butyl-isobutyramido)-5-ethyloxazole, b.p. 70°–72° C./0.2 mm.
2-(N-butyl-trifluoroacetamido)-4-methyloxazole, b.p. 67°–69° C./0.8 mm.

*Temperature recorded in an air-bath.
**Boiling point not taken but mass-spectral data in accord with structure.

Microanalysis (C,H,N) for each of the compounds listed in Examples 15 to 131 was (within the limits of experimental error) equal to the expected theoretical result. In addition, infra-red, ultra-violet and proton magnetic resonance spectra were consistent with the assigned structures.

All pressures measured in mm. of mercury.

I claim:

1. A compound of formula (III):

(III)

wherein $R^3$ and $R^4$ are independently selected from hydrogen, hydroxy, $C_{1-4}$ hydroxyalkyl, $C_{1-4}$ alkyl, $C_{3-8}$ cycloalkyl, $C_{3-6}$ acyloxyalkyl and phenyl optionally substituted by a halogen atom and wherein L is a group of formula —SOR or —SO$_2$R where R is benzyl or phenyl.

2. A compound according to claim 1, wherein $R^3$ is methyl and $R^4$ is hydrogen.

3. A compound of the formula

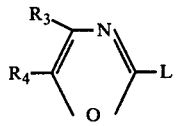

wherein $R^3$ and $R^4$ are independently selected from hydroxy, $C_{1-4}$ hydroxyalkyl, $C_{3-8}$ cycloalkyl and $C_{3-6}$ acyloxyalkyl, and wherein L is a group of the formula —SOR or —SO$_2$R where R is $C_{1-8}$ alkyl, $C_{3-8}$ cycloalkyl, benzyl or phenyl.

* * * * *